United States Patent
Daynes et al.

(10) Patent No.: US 6,813,517 B2
(45) Date of Patent: Nov. 2, 2004

(54) CONFIGURING DEFIBRILLATOR ENERGY DOSING

(75) Inventors: John C. Daynes, Redmond, WA (US); Richard M. Lee, Kirkand, WA (US)

(73) Assignee: Medtronic Physio-Control Corp., Redmond, WA (US)

( * ) Notice: Subject to any disclaimer, the term of this patent is extended or adjusted under 35 U.S.C. 154(b) by 386 days.

(21) Appl. No.: 10/012,635

(22) Filed: Nov. 6, 2001

(65) Prior Publication Data

US 2003/0088284 A1 May 8, 2003

(51) Int. Cl.[7] ................................................. A61N 1/39
(52) U.S. Cl. ........................................................ 607/7
(58) Field of Search ............................... 607/4–11, 34, 607/62, 74

(56) References Cited

U.S. PATENT DOCUMENTS

| | | | | |
|---|---|---|---|---|
| 4,823,796 A | * | 4/1989 | Benson | 607/7 |
| 4,830,006 A | * | 5/1989 | Haluska et al. | 607/4 |
| 5,111,813 A | * | 5/1992 | Charbonnier et al. | 607/8 |
| 5,230,336 A | | 7/1993 | Fain et al. | |
| 5,531,770 A | * | 7/1996 | Kroll et al. | 607/8 |
| 5,534,015 A | | 7/1996 | Kroll et al. | |
| 5,593,427 A | | 1/1997 | Gliner et al. | |
| 5,601,612 A | | 2/1997 | Gliner et al. | |
| 5,607,454 A | | 3/1997 | Cameron et al. | |
| 5,999,852 A | | 12/1999 | Elabbady et al. | |
| 6,101,413 A | * | 8/2000 | Olson et al. | 607/5 |
| 6,134,468 A | | 10/2000 | Morgan et al. | |
| 6,241,751 B1 | | 6/2001 | Morgan et al. | |
| 6,539,258 B1 | * | 3/2003 | Sullivan et al. | 607/7 |

* cited by examiner

*Primary Examiner*—George Manuel
(74) *Attorney, Agent, or Firm*—Shumaker & Sieffert, P.A.

(57) ABSTRACT

A defibrillator can be programmed with multiple energy protocols to be followed when the defibrillator administers therapy to a patient. Each energy protocol defines a sequence of energy dosages or levels to be applied during consecutive shocks. When the defibrillator is activated, the first energy dosage in the sequence is administered to the patient. If the first dosage is ineffective, the defibrillator administers subsequent dosages to the patient. Programming multiple energy protocols into the defibrillator allows the defibrillator to be adapted for use on a variety of patients with diverse needs, such as children and large adults, thereby improving the versatility of the defibrillator. Furthermore, because the expert responder can select the energy protocol most appropriate for the needs of the particular patient, therapy may be more effective.

33 Claims, 11 Drawing Sheets

AED MODE

SEQUENCE OF DEFIBRILLATION ENERGIES

| ENERGY PROTOCOL | 200 300 360 |
|---|---|
| VOICE PROMPTS | ON |
| AUTO ANALYZE | OFF |
| MOTION DETECTION | ON |
| ECG DISPLAY | ON |
| CPR TIME 1 | 60 SECONDS |
| CPR TIME 2 | 60 SECONDS |
| PREVIOUS PAGE | SERVICE |

| PRESET PROTOCOLS | LOW ENERGY |
|---|---|
| ENERGY 1 | 150 |
| ENERGY 2 | 175 |
| ENERGY 3 | 200 |
| PREVIOUS PAGE | |

CONFIGURING DEFIBRILLATOR ENERGY DOSING

TECHNICAL FIELD

The invention relates generally to defibrillators and, more specifically, to defibrillator control.

BACKGROUND

Ventricular fibrillation is a common and dangerous medical condition that causes the electrical activity of the human heart to become unsynchronized. Loss of synchronization may impair the natural ability of the heart to contract and pump blood throughout the body. Medical personnel treat ventricular fibrillation by using a defibrillator to apply an electrical current to the heart. The current flow overcomes the unsynchronized electrical activity and gives the natural pacing function of the heart an opportunity to recapture the heart and reestablish a normal sinus rhythm.

The appropriate energy dosage for a particular patient depends on a number of variables, including the body structure of the patient. A larger patient, for example, may exhibit greater electrical resistance through the thorax, known as transthoracic impedance, than a smaller patient. As a result, effective treatment of large patients tends to involve larger energy dosages. Large energy dosages, however, may traumatize the heart and cause discomfort to the patient. Accordingly, the American Heart Association (AHA) recommendation is an incremental approach to electrotherapy in which the heart initially receives a lower energy dosage. If required, an operator may increase the dosage by increments. For example, the recommended initial energy dosage for a patient may be 150 joules (J). If this dosage is ineffective, the operator may increase the dosage to 175 J and, subsequently, 200 J by adjusting a dosage setting of the defibrillator.

Electrotherapy may vary not only the electrical energy dosage applied to a patient, but also the morphology of the energy dosage waveform. Biphasic defibrillation involves passing a relatively large energy dosage across the heart in one direction, followed by a smaller energy dosage in the opposite direction. The initial dosage for biphasic defibrillation tends to be smaller than an earlier initial dosage for monophasic defibrillation. Biphasic defibrillation may involve incrementally increased energy dosages. Nevertheless, biphasic defibrillation can achieve results that are comparable to earlier monophasic defibrillation with lower energy dosages and reduced trauma to the heart.

Variations in the dosage energy and pattern, as well as other operating parameters, may make operating a defibrillator difficult, particularly for non-medical or minimally trained persons. Ease of operation has become an especially significant concern with the advent of portable defibrillation devices designed for use by first responders, who typically have little or no training. Such devices improve the likelihood of patient recovery by facilitating early administration of defibrillation, but require often untrained responders to be able to operate a complex medical device under stressful conditions.

SUMMARY

In general, the invention facilitates use of a defibrillator, such as an automated external defibrillator (AED), by allowing a user to select an energy protocol to be followed when the defibrillator administers therapy to a patient. More particularly, the defibrillator can be preprogrammed with multiple defibrillation energy protocols, or sequences of energy dosages, for delivery to the patient under appropriate circumstances.

Each energy protocol defines a sequence of energy dosages or levels to be applied during consecutive shocks. When the defibrillator is activated, the first, and typically lowest, energy dosage in the sequence is administered to the patient. The defibrillator then determines whether the first dosage was effective, that is, whether the patient was successfully defibrillated. If the first dosage was ineffective, a period of CPR is recommended to be undertaken in which the defibrillator administers the second dosage in the sequence to the patient. This second dosage is typically higher than the first dosage. The energy protocol may specify additional energy dosages to be applied if the first two dosages are ineffective, each followed by a period of CPR.

The invention may offer several advantages. Programming energy protocols into the defibrillator, for example, facilitates operation of the defibrillator by relieving an untrained or undertrained responder of the task of selecting individual energy dosages to be applied to a patient. With multiple energy protocols programmed, the defibrillator can be converted from one type of device, such as a pediatric defibrillator, to a different type of device, such as a high energy defibrillator, quickly. The versatility of the defibrillator is thereby enhanced. Furthermore, because the responder can select the energy protocol most appropriate for the needs of the particular patient, therapy may be more effective in comparison to some conventional defibrillators that lack the ability to deliver therapy in accordance with an operator-selectable regime.

In one embodiment, the invention is directed to a method in which at least two energy protocols are stored in a defibrillator. Each energy protocol comprises a sequence of energy dosages for application to a patient. A selected energy protocol is applied to the patient.

Another embodiment of the invention is directed to a method in which at least two energy protocols are programmed in a defibrillator. Each energy protocol defines a sequence of energy dosages for application to a patient. The energy protocols are stored in a memory associated with the defibrillator.

Other implementations include defibrillation systems that carry out these methods, as well as computer-readable media containing instructions that cause a computer to perform these methods. For example, in one embodiment, a defibrillation system includes a defibrillator and a memory communicatively coupled to the defibrillator. The memory stores at least two energy protocols. Each energy protocol comprises a sequence of energy dosages for application to a patient. The defibrillator applies a selected one of the energy protocols to the patient.

The details of one or more embodiments of the invention are set forth in the accompanying drawings and the description below. Other features, objects, and advantages of the invention will be apparent from the description and drawings, and from the claims.

BRIEF DESCRIPTION OF DRAWINGS

FIGS. 4–11 illustrate example user interfaces presented by the defibrillating system of FIG. 1.

DETAILED DESCRIPTION

Figure 1:
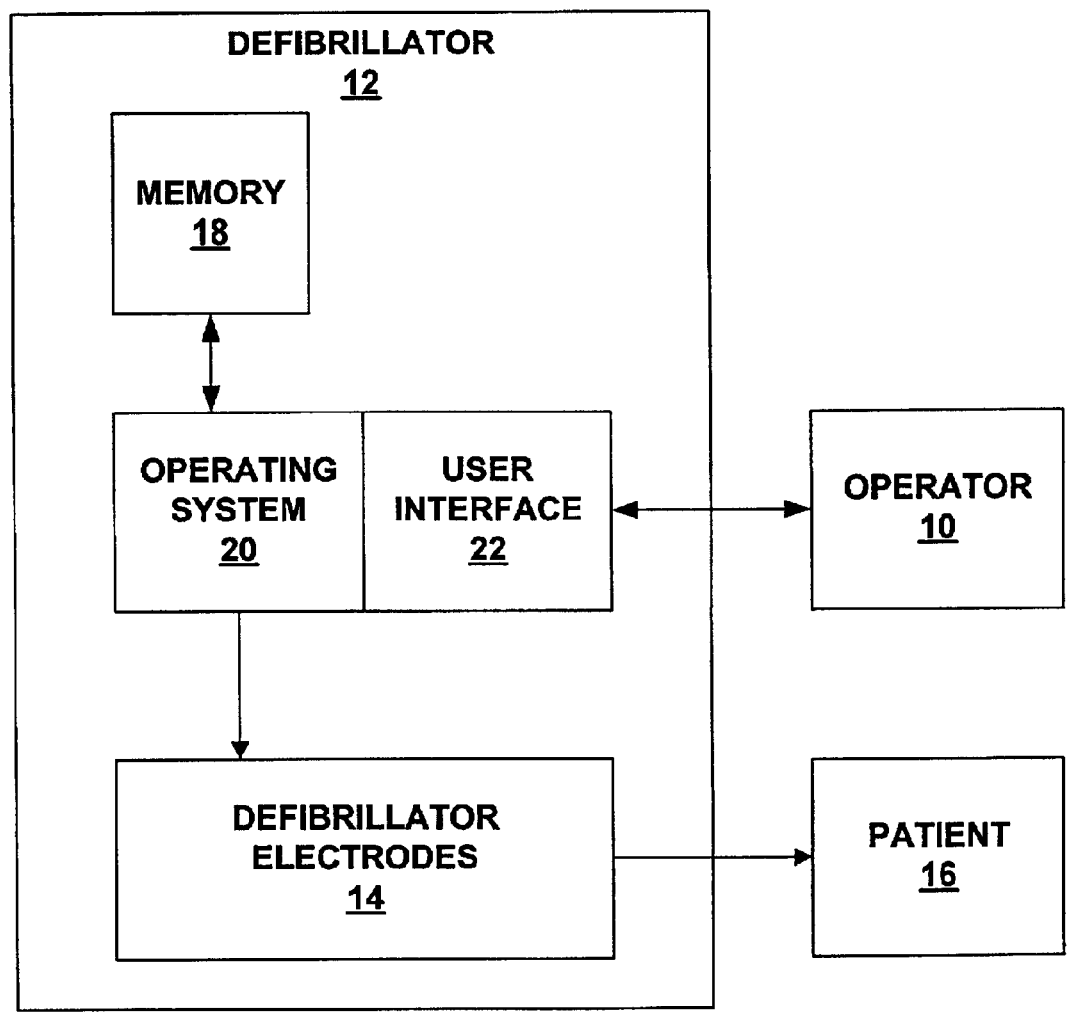
FIG. 1 is a block diagram illustrating a defibrillating system configured according to an embodiment of the invention.

FIG. 1 is a block diagram illustrating a defibrillating system in which the invention may be practiced. When activated by an operator 10, a defibrillator 12 administers one or more electric shocks via defibrillator electrodes 14 to a patient 16. Defibrillator 12 may be implemented, for example, as an automated external defibrillator (AED). Operator 10 may be a paramedic or other trained professional in rare occasions, but is more likely to be an inexperienced or undertrained first responder in an emergency. Accordingly, operator 10 is usually not adequately qualified to determine the energy dosages or levels that are best suited for the needs of the particular patient 16.

Defibrillator 12 includes a memory 18 that stores two or more defibrillation energy protocols. Memory 18 may be implemented, for example, using a random access memory (RAM) device. Each energy protocol defines a sequence of energy dosages or levels to be applied during consecutive shocks. When operator 10 activates defibrillator 12, the first, and typically lowest, energy dosage in the sequence is administered to patient 16. Defibrillator 12 then determines whether the first dosage was effective, i.e., whether patient 16 was successfully defibrillated. If defibrillation was unsuccessful, defibrillator 12 administers the second dosage in the sequence to patient 16. This second dosage is typically higher than the first dosage. The energy protocol may specify one or more additional energy dosages to be applied if the first two dosages are ineffective.

When defibrillator 12 is activated, an operating system 20 that controls the operation of defibrillator 12 reads a selected defibrillation energy protocol from memory 18. Operator may select this protocol when he or she activates defibrillator 12, but the protocol is usually selected in advance during a setup process. One of the energy protocols may be designated as a default energy protocol that is administered to patient 16 unless operator 10 selects a different energy protocol. In this manner, operator 10 can use defibrillator 12 with minimal set up under appropriate circumstances. On the other hand, when the default energy protocol is inappropriate for the particular needs of patient 16, an expert operator 10 can easily select a protocol that is more appropriate for patient 16. As a specific example, the default energy protocol may be a high energy protocol that may be harmful when administered to a child. Accordingly, the operator may select a pediatric energy protocol in which defibrillator 12 administers electric shocks of lower energy than would be administered to an adult. In some implementations, to further simplify operation of defibrillator 12, operator 10 may not be given the option to change the energy protocol dynamically.

Operating system 20 presents a user interface 22, described more fully below in connection with FIGS. 4–11, to assist operator 10 in selecting an appropriate energy protocol. Trained personnel may also define the energy protocols stored in memory 18 and may configure other operational parameters of defibrillator 12 via user interface 22. These energy protocols may include, but are not limited to, a low energy protocol, a high energy protocol, and a pediatric energy protocol. In the low energy protocol, for example, the highest energy dosage may be 200 Joules (J). By contrast, in the high energy protocol, defibrillator 12 may apply energy dosages of up to 360 J.

Operating system 20 and user interface 22 may be implemented as a set of computer-executable instructions stored in some form of computer readable media. Computer readable media can be any available media that can be accessed by defibrillator 12. By way of example, and not limitation, computer readable media may comprise computer storage media and communication media. Computer storage media includes volatile and nonvolatile, removable and nonremovable media implemented in any method or technology for storage of information, such as computer readable instructions, data structures, program modules, or other data. Computer storage media includes, but is not limited to, memory 18, read only memory (ROM), EEPROM, flash memory or other memory technology, CD-ROM, digital versatile discs (DVD) or other optical storage, magnetic cassettes, magnetic tape, magnetic disk storage or other magnetic storage devices, or any other medium that can be used to store the desired information and that can be accessed by defibrillator 12. Communication media typically embodies computer readable instructions, data structures, program modules, or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media, such as a wired network or other direct-wired connection, and wireless media, such as acoustic, RF, infrared, and other wireless media. Combinations of any of the above computer storage media and communication media are also included within the scope of computer-readable media. In some embodiments, the instructions may be stored in memory 18.

Allowing a setup technician to select an energy protocol to be administered to patient 16 facilitates operation of defibrillator 12 by relieving inexperienced or undertrained responders of the need to determine individual energy dosages to be applied to patient 16. Furthermore, with defibrillator 12 programmed with multiple energy protocols, defibrillator 12 can be converted quickly from one type of device, such as a pediatric defibrillator, to a different type of device, such as a high energy defibrillator. Defibrillator 12 can also be programmed to automatically convert itself from one type of device, such as a low energy defibrillator, to a different type of device, such as a high energy defibrillator, based on results obtained during device operation, without human intervention. Defibrillator 12 is thus more versatile than some conventional defibrillators that lack the ability to deliver therapy in accordance with an operator-selectable regime. In addition, because the responder can also manually select the energy protocol most appropriate for the needs of a particular type of patient, e.g., patients in a pediatric ward, therapy may be more effective.

Figure 2:
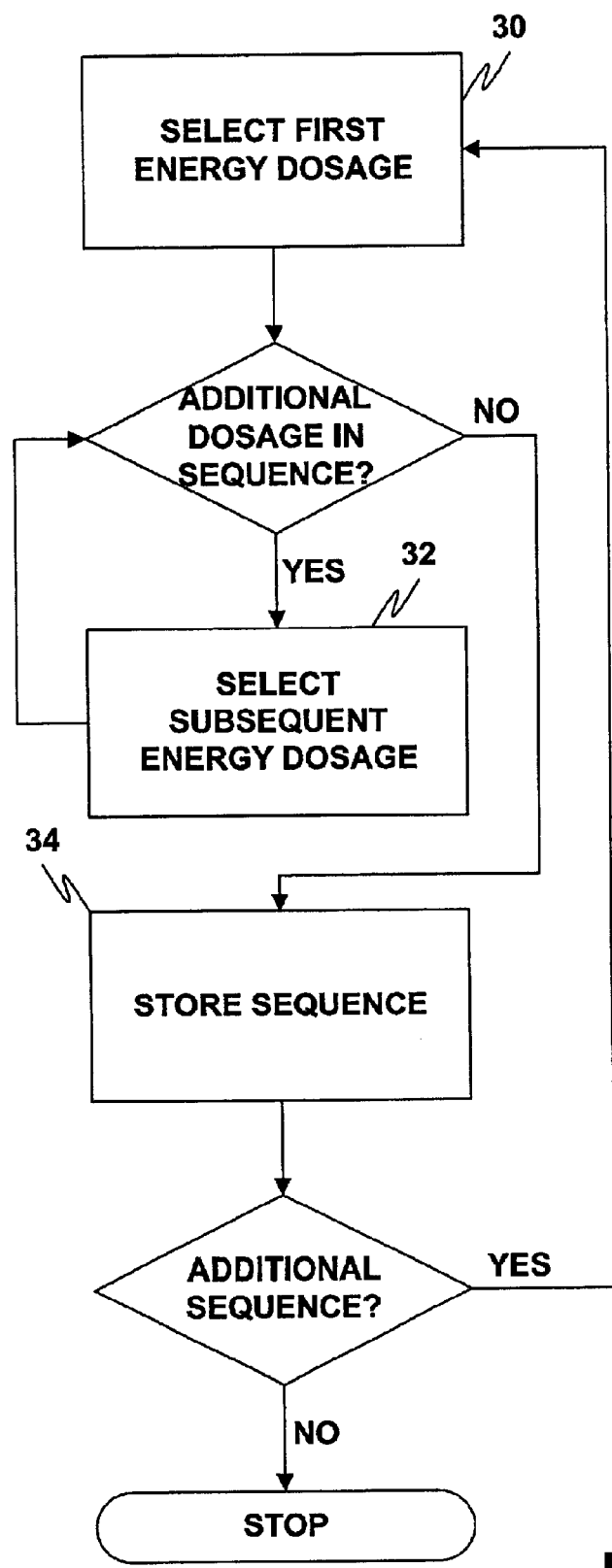
FIG. 2 is a flow diagram illustrating a first mode of operation of the defibrillating system of FIG. 1.

FIG. 2 is a flow diagram illustrating one mode of operation of defibrillator 12 in which an appropriately trained person configures defibrillator 12 for subsequent use. Defibrillator 12 is programmed with at least two energy protocols that define sequences of energy dosages for application to a patient. In particular, to define an energy protocol, the user selects an energy dosage to be administered during the first electric shock in the sequence (30). If the sequence is to include additional shocks to be administered if the first shock is unsuccessful, the user selects the subsequent energy dosage or dosages (32). Each energy protocol is usually a sequence of three energy dosages, but may include more or fewer energy dosages.

The user may specify the energy dosages by selecting from a set of preset values. Alternatively, the user may specify the energy dosages by entering values other than the preset values. Additionally, the user may specify the energy dosages by customizing a factory-defined energy protocol, i.e., by selecting the factory-defined energy protocol and adjusting one or more of the energy dosages within the factory-defined energy protocol.

When all energy dosages for the energy protocol have been selected, defibrillator 12 stores the energy protocol in memory 18. The user may then define another energy protocol. Alternatively, defibrillator 12 may wait to store the energy protocols in memory 18 until the user has defined all of the energy protocols.

Figure 3:
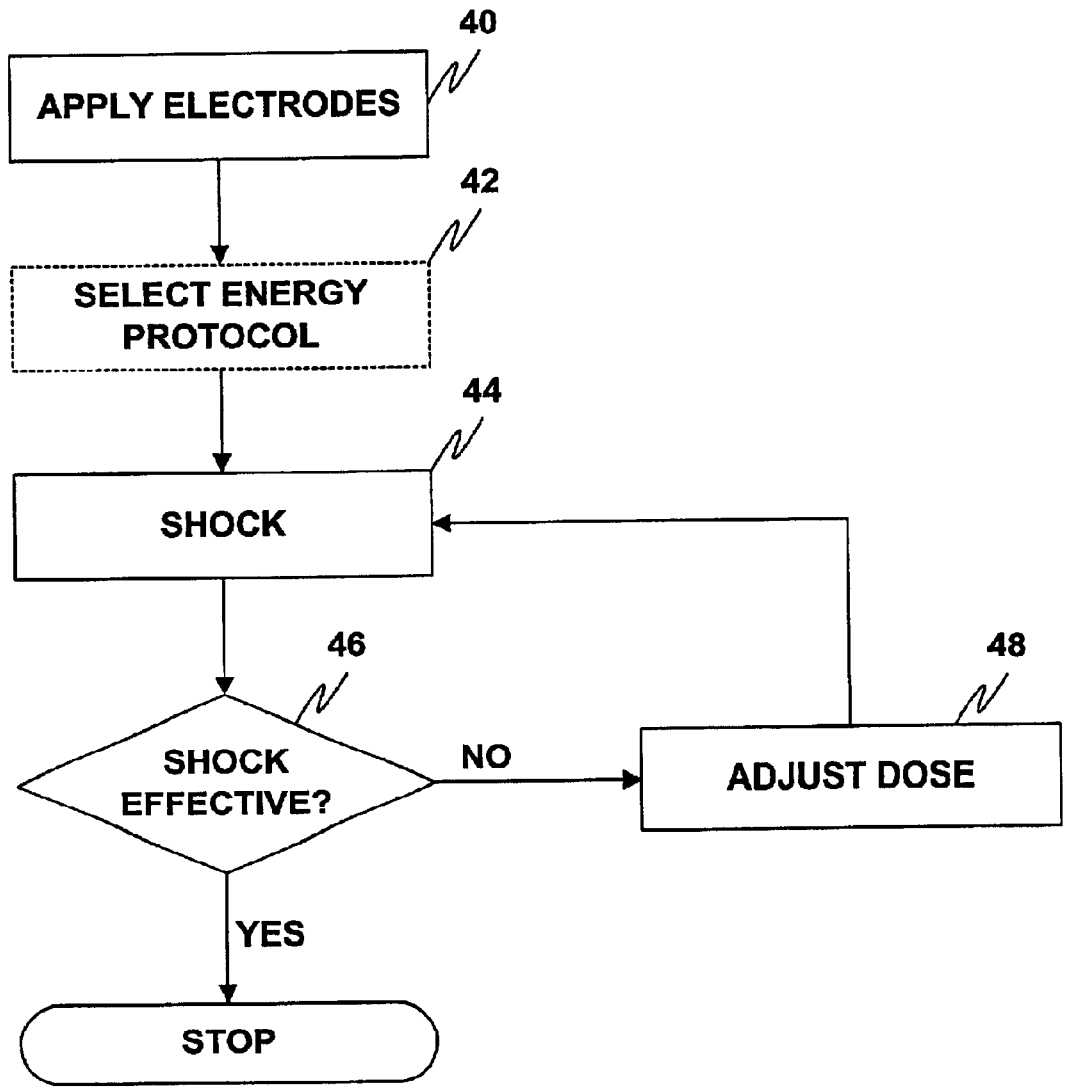
FIG. 3 is a flow diagram illustrating a second mode of operation of the defibrillating system of FIG. 1.

After defibrillator 12 has been programmed in this way, it is ready for use in delivering defibrillation therapy. FIG. 3 is a flow diagram illustrating another mode of operation of defibrillator 12 in which operator 10 administers defibrillation therapy to patient 16. Operator 10 positions defibrillator electrodes 14 at appropriate locations on patient 16 (40). Operator 10 may then either use the default energy protocol, or optionally may select an alternative energy protocol (42). As described above, some implementations may not allow operator 10 to select an alternative energy protocol, thereby further simplifying operation of defibrillator 12.

Defibrillator 12 then administers a shock at the first energy dosage (44). Operator 10 may manually trigger defibrillator 12 to administer the shock. In some embodiments, defibrillator 12 may automatically sense placement of defibrillation electrodes 14 on patient 16 and administer the shock without intervention by operator 10 when appropriate. In either case, defibrillator 12 evaluates the condition of patient 16 to determine whether the first shock was effective or whether another shock is required (46). If the first shock was effective, therapy ends, and defibrillator 12 does not administer subsequent shocks. If, on the other hand, the first shock failed to defibrillate patient 16, defibrillator 12 automatically adjusts the energy dosage to the second level specified in the energy protocol (48) and delivers another shock (44). If operator 10 is appropriately trained, he or she can make the determination of whether to administer additional shocks and may override the determination of defibrillator 12.

After delivering the second shock, defibrillator 12 or operator 10 determines whether the second shock was effective, or whether an additional shock is indicated (46). If another shock is indicated, defibrillator 12 adjusts the energy dosage to the third level specified in the energy protocol (48) and delivers another shock (44). The process of evaluating patient 16, adjusting the energy dosage, and delivering a shock at the adjusted dosage may be repeated until patient 16 is successfully defibrillated or until it is otherwise medically advisable to end therapy. If defibrillator 12 reaches the end of the sequence of energy dosages without successfully defibrillating patient 16, defibrillator 12 may continue to deliver subsequent shocks at the last energy dosage in the sequence.

In some embodiments of the invention, operator 10 may optionally adjust the energy dosage to be administered during a particular defibrillation attempt. Adjusting the energy dosages in this manner, however, may present a risk to patient 16 if not done properly. Accordingly, this option may not be advisable if operator 10 is inexperienced or undertrained.

Figure 4:
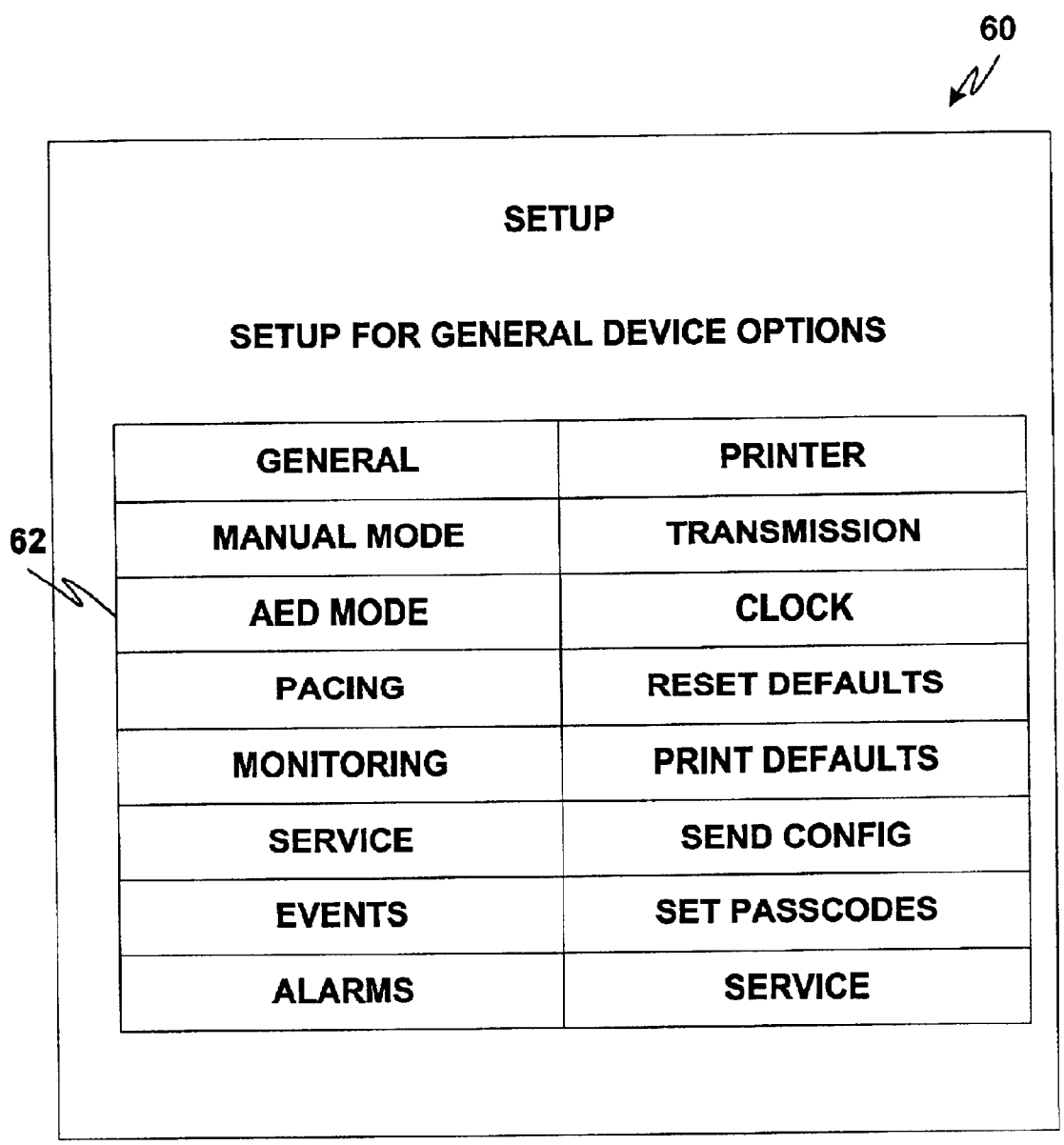

As described above in connection with FIG. 1, user interface 22 may be used to configure various operational parameters of defibrillator 12. FIG. 4 illustrates an example setup menu 60 that may be presented by user interface 22 to configure defibrillator 12. User interface 22 may take the form of a display screen and input media, such as a keypad or touchscreen, which are integrated with defibrillator 12. A user may access the screen to configure a variety of functions for defibrillator 12. For example, the user may select a menu item 62 to configure the default energy protocol by specifying the default sequence of energy dosages to be administered.

When the user selects menu item 62, user interface 22 displays an AED mode summary screen 64 of the current AED settings, as illustrated in FIG. 5. In the particular AED mode summary screen 64 depicted in FIG. 5, for example, an energy protocol indicator 66 shows that the preset energy levels are currently set to 150 J, 175 J, and 200 J, respectively.

Figure 6:
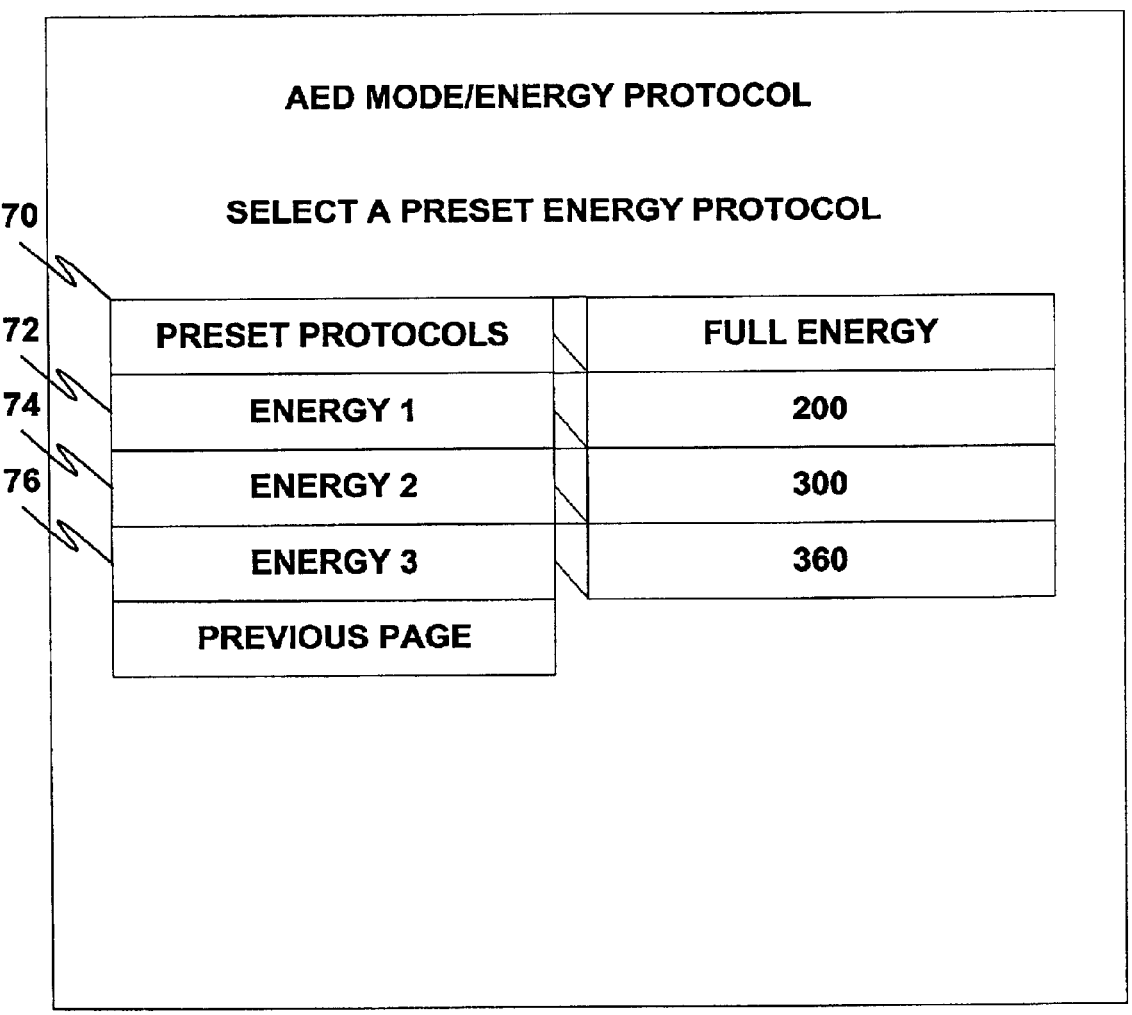

The user may modify these settings by selecting energy protocol indicator 66, causing user interface 22 to display an energy protocol configuration screen 68, illustrated in FIG. 6. A menu item 70 indicates which energy protocol is currently displayed. As shown in FIG. 6, the "Full Energy" protocol is displayed. Additional menu items 72, 74, and 76 indicate the energy dosages for the first, second, and third defibrillation shocks, respectively.

The user may select menu item 70 to specify which energy protocol to configure. When the user selects menu item 70, a pull-down menu 78, depicted in FIG. 7, displays the set of available energy protocols that can be configured. The user then selects one of the available energy protocols, causing user interface 22 to display another energy protocol configuration screen 80, as illustrated in FIG. 8.

Figure 7:
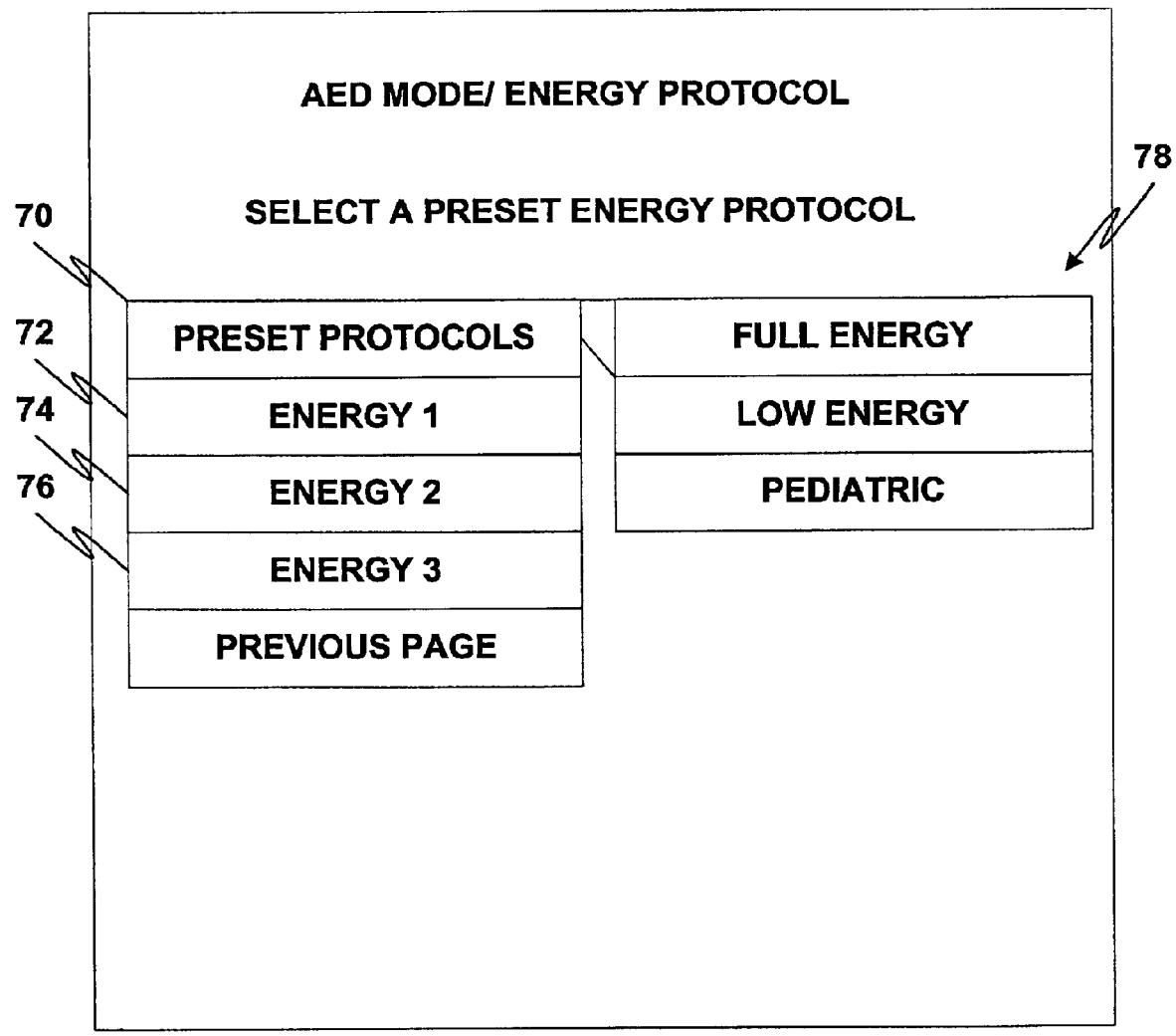
Figure 8:
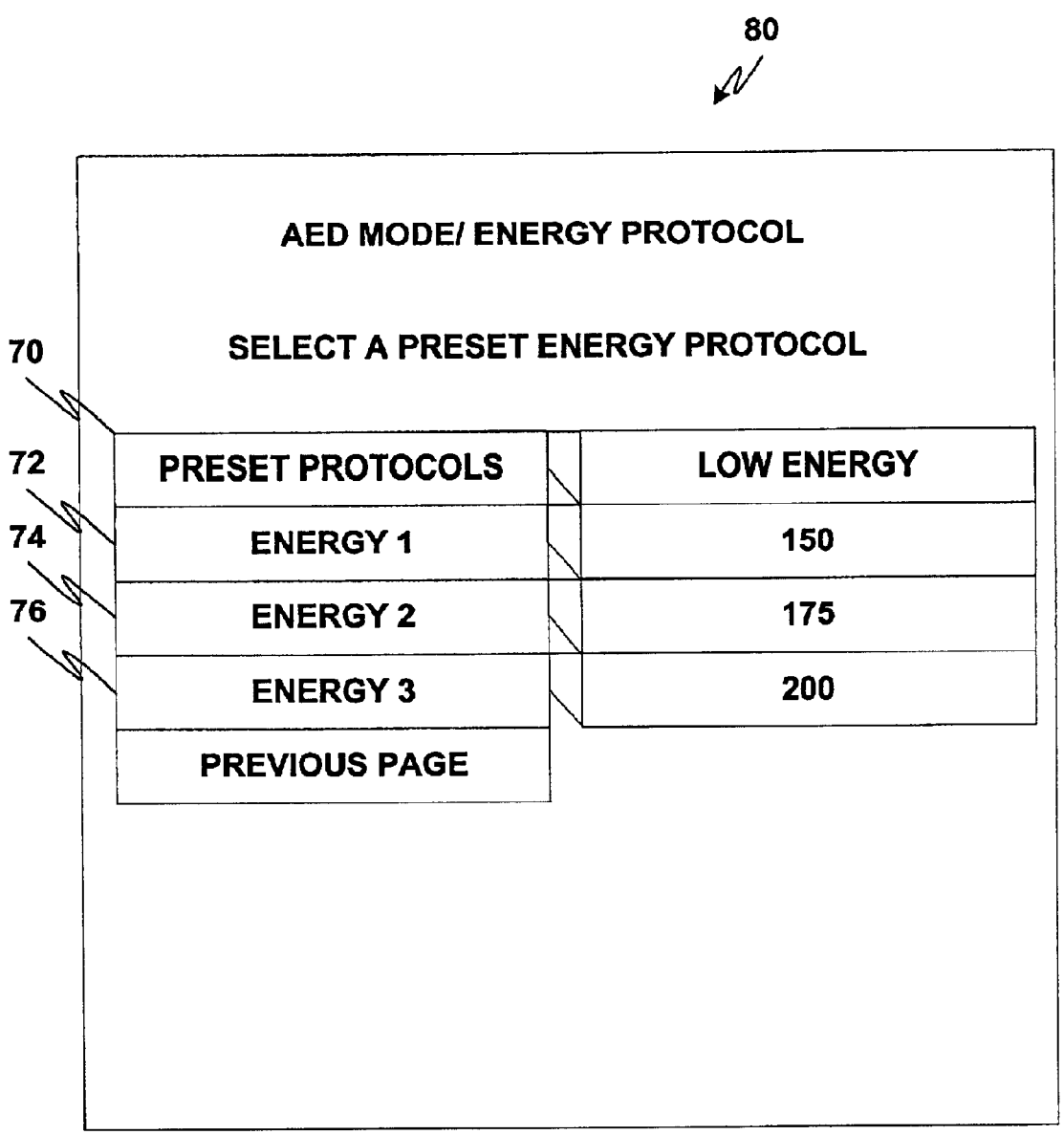

FIG. 8 depicts the energy protocol configuration screen 80 that is displayed when the user selects the "Low Energy" protocol from pull-down menu 78 of FIG. 7. As with energy protocol configuration screen 68 of FIG. 6, menu items 72, 74, and 76 indicate the energy dosages for the selected energy protocol. Energy protocol configuration screen 80 of FIG. 8 shows these energy dosages as 150 J, 175 J, and 200 J. The user may accept these values, or may adjust one or more of the values by selecting one or more of menu items 72, 74, and 76.

Figure 9:
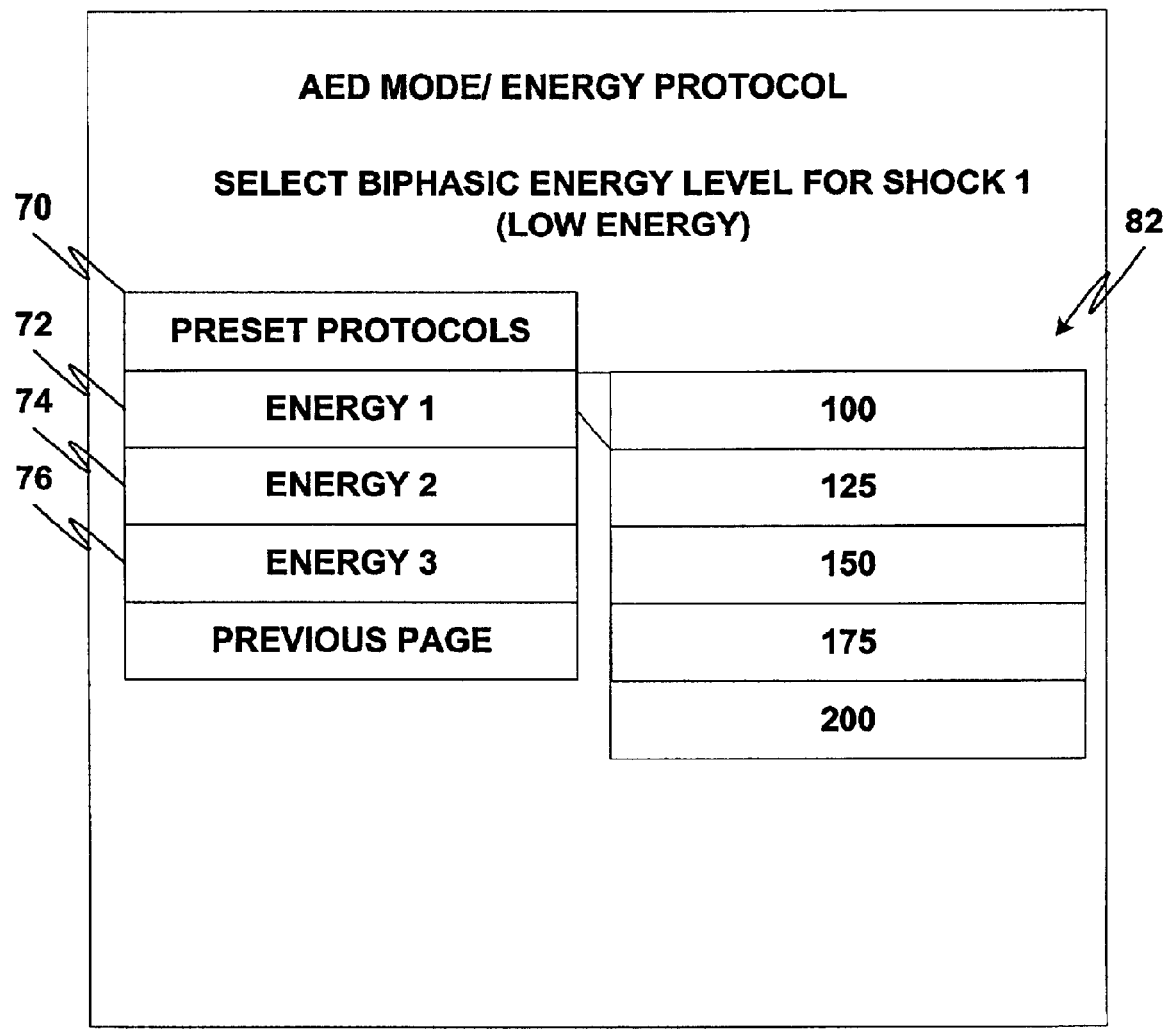
Figure 10:
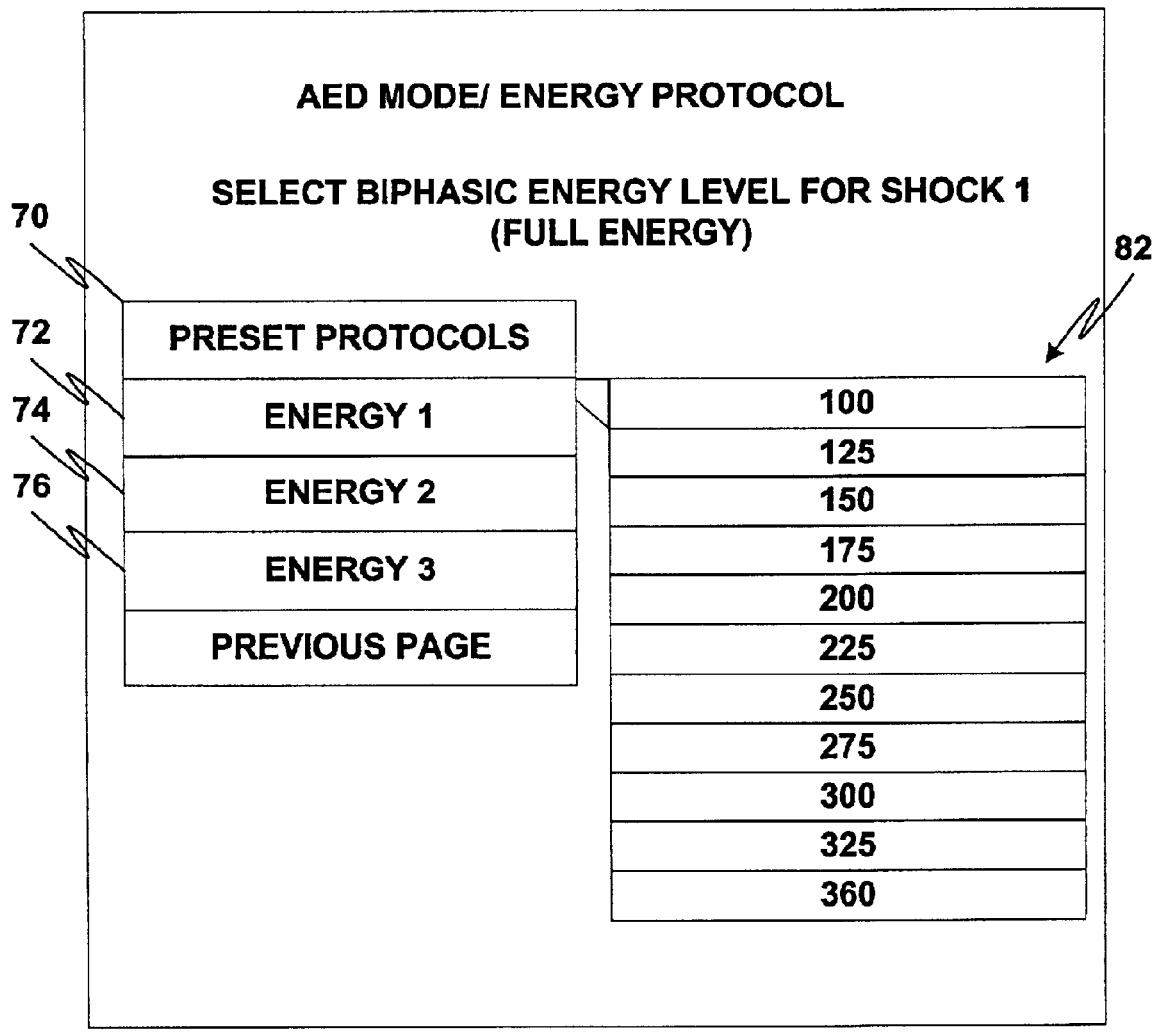
Figure 11:

FIG. 9 illustrates an energy dosage pull-down menu 82 that is presented when the user selects menu item 72 to specify the first energy dosage in the "Low Energy" protocol. In the pull-down menu 82 shown in FIG. 9, the user can select energy dosages between 100 J and 200 J for the "Low Energy" protocol. By contrast, in the pull-down menu 82 shown in FIG. 10 for the "Full Energy" protocol, the user can select energy dosages between 100 J and 360 J. Accordingly, the range of energy dosages that are available to the user may vary according to the user-selectable energy protocol.

When the user has finished defining the energy dosages for the selected energy protocol, user interface 22 presents a summary screen 84 that indicates the selected energy protocol and the energy dosages set for each defibrillation shock in the sequence.

Various embodiments of the invention have been described. These and other embodiments are within the scope of the following claims. For example, as described above, the invention is not limited to a specific number of energy levels, nor is the invention limited to specific energy settings or ranges of settings overall or within a given energy level. The invention may be used in AEDs as well as other types of defibrillators.

What is claimed is:

1. A method comprising:

storing at least two defibrillation energy protocols in a defibrillator, each defibrillation energy protocol comprising a sequence of defibrillation energy dosages for application to a patient;

defining one of the stored defibrillation energy protocols as a default defibrillation energy protocol in response to a selection from a user; and applying defibrillation energy dosages to the patient according to the sequence defined by the default energy protocol selected by the user.

2. The method of claim 1, wherein the default defibrillation energy protocol selected by the user comprises a sequence of biphasic defibrillation energy dosages to be applied to the patient.

3. The method of claim 1, further comprising:

applying to the patient a first defibrillation energy dosage in the default defibrillation energy protocol selected by the user;

determining whether the first defibrillation energy dosage successfully defibrillated the patient; and when the first defibrillation energy dosage did not successfully defibrillate the patient, applying to the patient a second defibrillation energy dosage in the default defibrillation energy protocol selected by the user.

4. The method of claim 3, further comprising:

determining whether the second defibrillation energy dosage successfully defibrillate the patient; and when the second defibrillation energy dosage did not successfully defibrillate the patient, applying a third defibrillation energy dosage in the default defibrillation energy protocol selected by the user.

5. The method of claim 1, wherein the default defibrillation energy protocols selected by the user comprises a pediatric defibrillation energy protocol.

6. The method of claim 1, wherein the default defibrillation energy protocols selected by the user comprises a low energy defibrillation protocol.

7. The method of claim 1, wherein the default defibrillation energy protocols selected by the user comprises a high energy defibrillation protocol.

8. A method comprising:

programming at least two defibrillation energy protocols in a defibrillator, each defibrillation energy protocol comprising a sequence of defibrillation energy dosages for application to a patient;

storing the defibrillation energy protocols in a memory associated with the defibrillator; and defining one of the stored defibrillation energy protocols as a default defibrillation energy protocol in response to a selection from a user.

9. The method of claim 8, wherein the default defibrillation energy protocol selected by the user comprises a sequence of biphasic energy dosages to be applied to the patient.

10. The method of claim 8, wherein the default defibrillation energy protocols selected by the user comprises a pediatric defibrillation energy protocol.

11. The method of claim 8, wherein the default defibrillation energy protocols selected by the user comprises a low energy defibrillation protocol.

12. The method of claim 8, wherein the default defibrillation energy protocols selected by the user comprises a high energy defibrillation protocol.

13. The method of claim 8, further comprising applying defibrillation energy dosages to the patient according to the sequence defined by the default defibrillation energy protocol selected by the user.

14. A defibrillating system comprising:

a defibrillator; and a memory communicatively coupled to the defibrillator and configured to store at least two defibrillation energy protocols, each defibrillation energy protocol comprising a sequence of defibrillation energy dosages for application to a patient, wherein the defibrillator defines one of the stored defibrillation energy protocols as a default defibrillation energy protocol in response to a selection from a user, and applies defibrillation energy dosages to the patient according to the sequence defined by the default defibrillation energy protocol selected by the user.

15. The defibrillating system of claim 14, wherein the default defibrillation energy protocol selected by the user comprises a sequence of biphasic defibrillation energy dosages to be applied to the patient.

16. The defibrillating system of claim 14, wherein the defibrillator is further configured to:

apply to the patient a first defibrillation energy dosage in the default defibrillation energy protocol selected by the user;

determine whether the first defibrillation energy dosage successfully defibrillated the patient; and when the first defibrillation energy dosage did not successfully defibrillate the patient, apply to the patient a second defibrillation energy dosage in the default defibrillation energy protocol selected by the user.

17. The defibrillating system of claim 16, wherein the defibrillator is further configured to:

determine whether the second defibrillation energy dosage successfully defibrillated the patient; and when the second defibrillation energy dosage did not successfully defibrillate the patient, apply to the patient a third defibrillation energy dosage in the default defibrillation energy protocol selected by the user.

18. The defibrillating system of claim 14, wherein the default defibrillation energy protocols selected by the user comprises a pediatric defibrillation energy protocol.

19. The defibrillating system of claim 14, wherein the default defibrillation energy defibrillation protocols selected by the user comprises a low energy defibrillation protocol.

20. The defibrillating system of claim 14, wherein the default defibrillation energy defibrillation protocols selected by the user comprises a high energy defibrillation protocol.

21. A computer-readable medium comprising computer executable instructions for:

storing at least two defibrillation energy protocols in a defibrillator, each defibrillation energy protocol comprising a sequence of defibrillation energy dosages for application to a patient;

defining one of the stored defibrillation energy protocols as a default defibrillation energy protocol in response to a selection from a user; and applying defibrillation energy dosages to the patient according to the sequence defined by the default energy defibrillation protocol selected by the user.

22. The computer-readable medium of claim 21, wherein the default defibrillation energy protocol selected by the user comprises a sequence of biphasic defibrillation energy dosages to be applied to the patient.

23. The computer-readable medium of claim 21, further comprising computer executable instructions for:
   applying to the patient a first defibrillation energy dosage in the default defibrillation energy protocol selected by the user;
   determining whether the first defibrillation energy dosage successfully defibrillated the patient; and
   when the first defibrillation energy dosage did not successfully defibrillate the patient, applying to the patient a second defibrillation energy dosage in the default defibrillation energy protocol selected by the user.

24. The computer-readable medium of claim 23, further comprising computer executable instructions for:
   determining whether the second defibrillation energy dosage successfully defibrillated the patient; and
   when the second defibrillation energy dosage did not successfully defibrillate the patient, applying a third defibrillation energy dosage in the default defibrillation energy protocol selected by the user.

25. The computer-readable medium of claim 21, wherein the default defibrillation energy protocols selected by the user comprises a pediatric defibrillation energy protocol.

26. The computer-readable medium of claim 21, wherein the default defibrillation energy protocols selected by the user comprises a low energy defibrillation protocol.

27. The computer-readable medium of claim 21, wherein the default defibrillation energy protocols selected by the user comprises a high energy defibrillation protocol.

28. A computer-readable medium comprising computer executable instructions for:
   programming at least two defibrillation energy protocols in a defibrillator, each defibrillation energy protocol comprising a sequence of defibrillation energy dosages for application to a patient;
   storing the defibrillation energy protocols in a memory associated with the defibrillator; and
   defining one of the stored defibrillation energy protocols as a default energy protocol in response to a selection from a user.

29. The computer-readable medium of claim 28, wherein the default defibrillation energy protocol selected by the user comprises a sequence of biphasic defibrillation energy dosages to be applied to the patient.

30. The computer-readable medium of claim 28, wherein the default defibrillation energy protocol selected by the user comprises a pediatric defibrillation energy protocol.

31. The computer-readable medium of claim 28, wherein the default defibrillation energy protocols selected by the user comprises a low energy defibrillation protocol.

32. The computer-readable medium of claim 28, wherein the default defibrillation energy protocols selected by the user comprises a high energy defibrillation protocol.

33. The computer-readable medium of claim 28, further comprising computer executable instructions for applying defibrillation energy dosages to the patient according to the sequence defined by the default defibrillation energy protocol selected by the user.

* * * * *

UNITED STATES PATENT AND TRADEMARK OFFICE
CERTIFICATE OF CORRECTION

PATENT NO. : 6,813,517 B2 Page 1 of 1
APPLICATION NO. : 10/012635
DATED : November 2, 2004
INVENTOR(S) : John C. Daynes and Richard M. Lee It is certified that error appears in the above-identified patent and that said Letters Patent is hereby corrected as shown below:

On column 7, line 30 (claim 4): "successfully defibrillate" should read --successfully defibrillated--.

On column 7, line 40 (claim 6): "energy protocols selected" should read --energy protocol selected--.

On column 7, line 43 (claim 7): "energy protocols selected" should read --energy protocol selected--.

On column 8, line 46 (claim 19): "energy defibrillation protocols selected" should read -- energy protocol selected--.

Signed and Sealed this

First Day of August, 2006

JON W. DUDAS
*Director of the United States Patent and Trademark Office*